(12) United States Patent
Boudin et al.

(10) Patent No.: US 10,057,513 B2
(45) Date of Patent: Aug. 21, 2018

(54) FLASH THERMOGRAPHY DEVICE FOR INSPECTING TURBINE COMPONENTS

(71) Applicant: Siemens Energy, Inc., Orlando, FL (US)

(72) Inventors: Dustin C. Boudin, Belmont, NC (US); Clifford Hatcher, Jr., Orlando, FL (US); Anand A. Kulkarni, Charlotte, NC (US); Kevin Licata, Belmont, NC (US)

(73) Assignee: SIEMENS ENERGY, INC., Orlando, FL (US)

( * ) Notice: Subject to any disclaimer, the term of this patent is extended or adjusted under 35 U.S.C. 154(b) by 135 days.

(21) Appl. No.: 15/180,364

(22) Filed: Jun. 13, 2016

(65) Prior Publication Data
US 2017/0359530 A1    Dec. 14, 2017

(51) Int. Cl.
*H04N 5/33*    (2006.01)
*H04N 5/225*    (2006.01)

(52) U.S. Cl.
CPC ........... *H04N 5/332* (2013.01); *H04N 5/2256* (2013.01)

(58) Field of Classification Search
CPC .............................. H04N 5/332; H04N 5/2256
See application file for complete search history.

(56) References Cited

U.S. PATENT DOCUMENTS

| 2005/0056786 | A1 | 3/2005 | Shepard et al. | |
| 2007/0217672 | A1* | 9/2007 | Shannon | G06T 7/0006 382/152 |
| 2013/0230072 | A1* | 9/2013 | Couse | G01N 25/72 374/5 |
| 2013/0258314 | A1* | 10/2013 | Gomi | G01J 3/12 356/51 |
| 2013/0335530 | A1* | 12/2013 | Hatcher, Jr. | G02B 23/2484 348/46 |

OTHER PUBLICATIONS

PCT International Search Report and Written Opinion of International Searching Authority dated Aug. 23, 2017 corresponding to PCT International Application No. PCT/US2017/034968, filed May 30, 2017.

* cited by examiner

*Primary Examiner* — Michael Teitelbaum

(57) ABSTRACT

A flash thermography device for generating an infrared image of a turbine component located inside a turbine. The device includes a flash enclosure having an aperture. A flash source is located in the aperture wherein the flash source generates a light pulse that heats the turbine component. The device also includes an infrared sensor for detecting thermal energy radiated by the turbine component wherein the radiated thermal energy is transmitted through the aperture to the infrared sensor to enable generation of an infrared image of the turbine component.

15 Claims, 5 Drawing Sheets

FLASH THERMOGRAPHY DEVICE FOR INSPECTING TURBINE COMPONENTS

FIELD OF THE INVENTION

This invention relates to flash thermography devices used in connection with turbines, and more particularly, to a flash thermography device having a flash enclosure that includes a flash source for heating a turbine component wherein the device also includes an infrared sensor for detecting thermal energy radiated by the turbine component to enable generation of an infrared image of the turbine component.

BACKGROUND OF THE INVENTION

In various multistage turbomachines used for energy conversion, such as gas turbines, a fluid is used to produce rotational motion. Referring to FIGS. 1 and 2, side and perspective partial cross sectional views of an axial flow gas turbine 10 is shown. The turbine 10 includes a compressor section 12, a combustion section 14 and a turbine section 16 arranged along a horizontal center axis 18. The combustion section 14 includes a plurality of combustors 28 arrayed about the combustion section 14 that are in fluid communication with a combustion section 14 interior. Each combustor 28 includes a top hat portion 30 and a removable support housing 32. The compressor section 12 provides a compressed air flow to the combustion section 14 where the air is mixed with a fuel, such as natural gas, and ignited to create a hot working gas. The turbine section 16 includes a plurality of turbine blades 20 arranged in a plurality of rows. The hot gas expands through the turbine section 16 where it is directed across the rows of blades 20 by associated stationary vanes 22. The blades 20 are each configured as a blade assembly that is attached to a shaft that is rotatable about the center axis 18. As the hot gas passes through the turbine section 16, the gas causes the blades 20 and thus the shaft to rotate, thereby providing mechanical work. Each row of blades 20 and associated vanes 22 (i.e. collectively, "airfoils") form a stage. In particular, the turbine section 16 may include four rows of blades 20 and associated rows of vanes 22 to form four stages. The gas turbine 10 further includes an exhaust cylinder section 24 located adjacent the turbine section 16 and an outer diffuser section 26 located adjacent the exhaust cylinder section 24.

Sections of the turbine 10 that are exposed to the hot gases as the gases travel along a hot gas path in the turbine 10 may include a ceramic-based coating that serves to minimize exposure of the base metal of a component, such as an airfoil base metal, to high temperatures that may lead to oxidation of the base metal. Such a coating may be a known thermal barrier coating (TBC) that is applied onto a bond coating (BC) formed on the base metal.

A turbine 10 is typically operated for extended periods. The TBC layer or both the TBC and BC layers may undesirably deteriorate or delaminate during operation of the turbine 10. This exposes the base metal to high temperatures, which may lead to oxidation of the base metal. A turbine is inspected at periodic intervals to check for wear, damage and other undesirable conditions that may have occurred with respect to various internal components. In addition, the TBC/BC layers are inspected to determine the degree of deterioration of the TBC/BC layers (i.e. remaining thickness of the layers) and other undesirable conditions. In order to inspect components within the turbine 10, the turbine 10 is shut down and allowed to cool down, which takes a substantial amount of time. An inspection/evaluation team must then disassemble substantial portions of the turbine 10, such as an outer casing 34 and associated components, in order to gain access to a desired internal turbine component and perform an assessment or inspection of the turbine component. However, the current procedure for inspection is labor intensive, time consuming and expensive.

SUMMARY OF INVENTION

A flash thermography device for generating an infrared image of a turbine component located inside a turbine is disclosed. The device includes a flash enclosure having an aperture. A flash source is located in the aperture wherein the flash source generates a light pulse that heats the turbine component. The device also includes an infrared sensor for detecting thermal energy radiated by the turbine component wherein the radiated thermal energy is transmitted through the aperture to the infrared sensor to enable generation of an infrared image of the turbine component.

Those skilled in the art may apply the respective features of the present invention jointly or severally in any combination or sub-combination.

BRIEF DESCRIPTION OF DRAWINGS

The teachings of the present disclosure can be readily understood by considering the following detailed description in conjunction with the accompanying drawings, in which.

To facilitate understanding, identical reference numerals have been used, where possible, to designate identical elements that are common to the figures.

DETAILED DESCRIPTION

Figure 1:
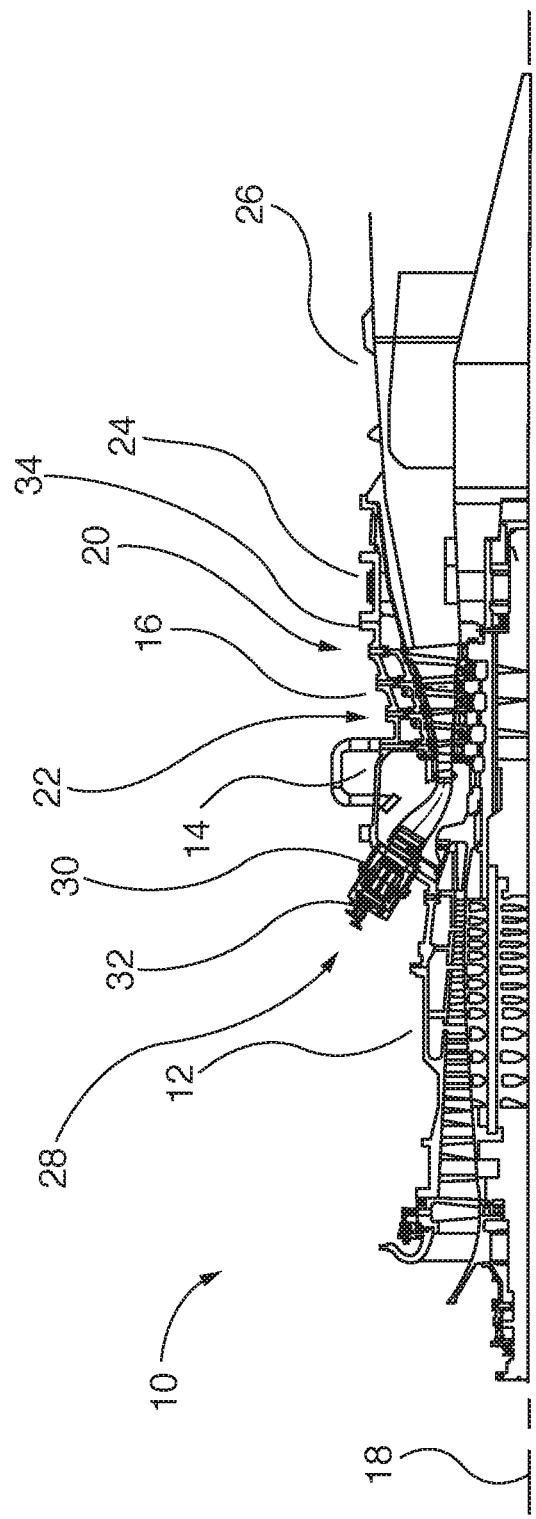
FIG. 1 is a side partial cross sectional view of an axial flow gas turbine.
Figure 2:
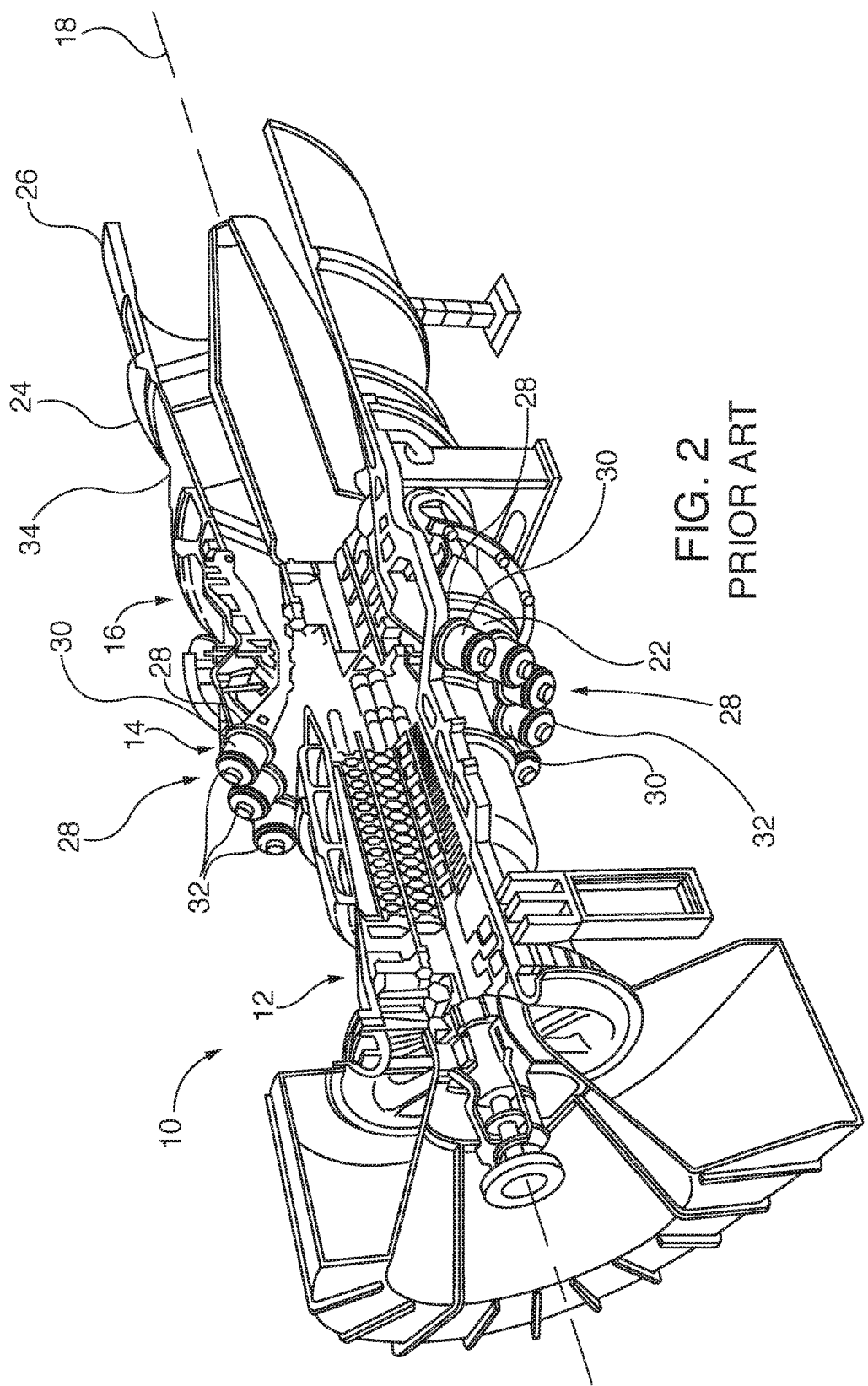
FIG. 2 is a perspective partial cross sectional view of an axial flow gas turbine.

Although various embodiments that incorporate the teachings of the present disclosure have been shown and described in detail herein, those skilled in the art can readily devise many other varied embodiments that still incorporate these teachings. The scope of the disclosure is not limited in its application to the exemplary embodiment details of construction and the arrangement of components set forth in the description or illustrated in the drawings. The disclosure encompasses other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "mounted," "connected," "supported," and "coupled" and variations thereof are used broadly and encompass direct and indirect mountings, connections, supports, and couplings. Further, "connected" and "coupled" are not restricted to physical or mechanical connections or couplings.

Figure 3:
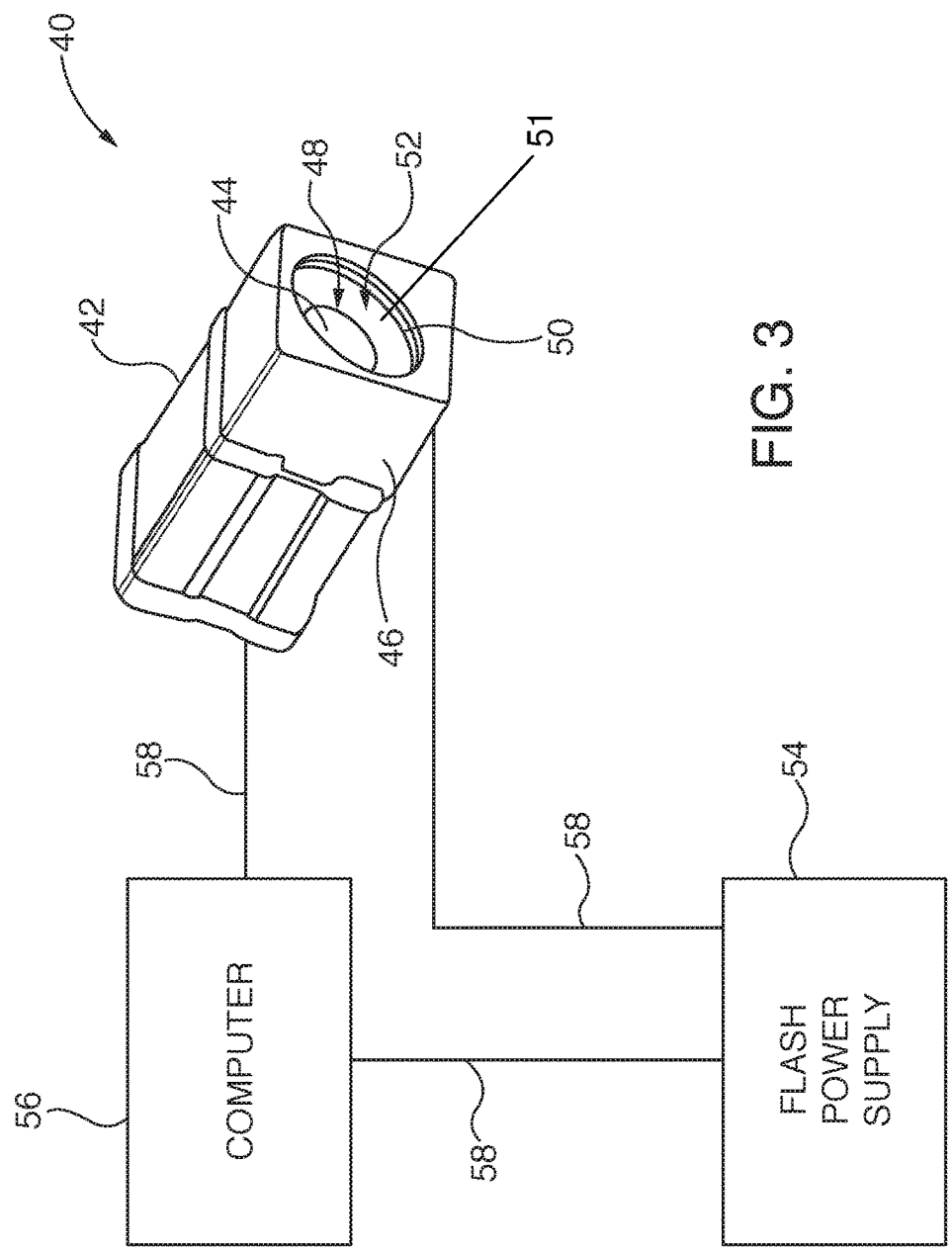
FIG. 3 depicts a flash thermography device for imaging a turbine component in accordance with an embodiment of the invention.

Referring to FIG. 3, a flash thermography device 40 for imaging a turbine component in accordance with an embodiment of the invention is shown. The device 40 includes an infrared (IR) sensor portion 42 for detecting thermal energy in the infrared region of the electromagnetic spectrum. In an embodiment, the IR sensor 42 is an IR camera having a lens 44 although it is understood that other types of IR sensors may be used. By way of example, the IR sensor 42 may be an IR camera such as that available from FLIR Systems, Boston, Mass., US.

The device 40 also includes a flash enclosure 46 having an enclosure aperture 48 that exposes the lens 44 to enable detection of thermal energy by the IR sensor 42. A flash source 50 is located around a periphery of the enclosure aperture 48. In an embodiment, the flash source 50 has an annular shape that includes a flash aperture 52 that is aligned with the enclosure aperture 48 and the lens 44. The flash source 50 may be configured as a flash tube although it is understood that other types of flash sources may be used. The flash enclosure 46 may also include a substantially cone shaped reflector 51. The device 40 further includes a flash power supply 54 connected between a computer 56 and the flash source 50 by electrical connections 58. The flash source 50 is energized by the flash power supply 54 thereby causing the flash source 50 to emit a light pulse that heats a component, such as a turbine component. A portion of the thermal energy radiated by the component travels through the enclosure 48 and flash 52 apertures and is detected by the IR sensor 42. The IR sensor 42 generates IR images of the component based on the thermal energy radiated by the component. The IR sensor 42 may also be configured to obtain image data at other frequencies in addition to or in place of the infrared region of the electromagnetic spectrum.

Figure 4:
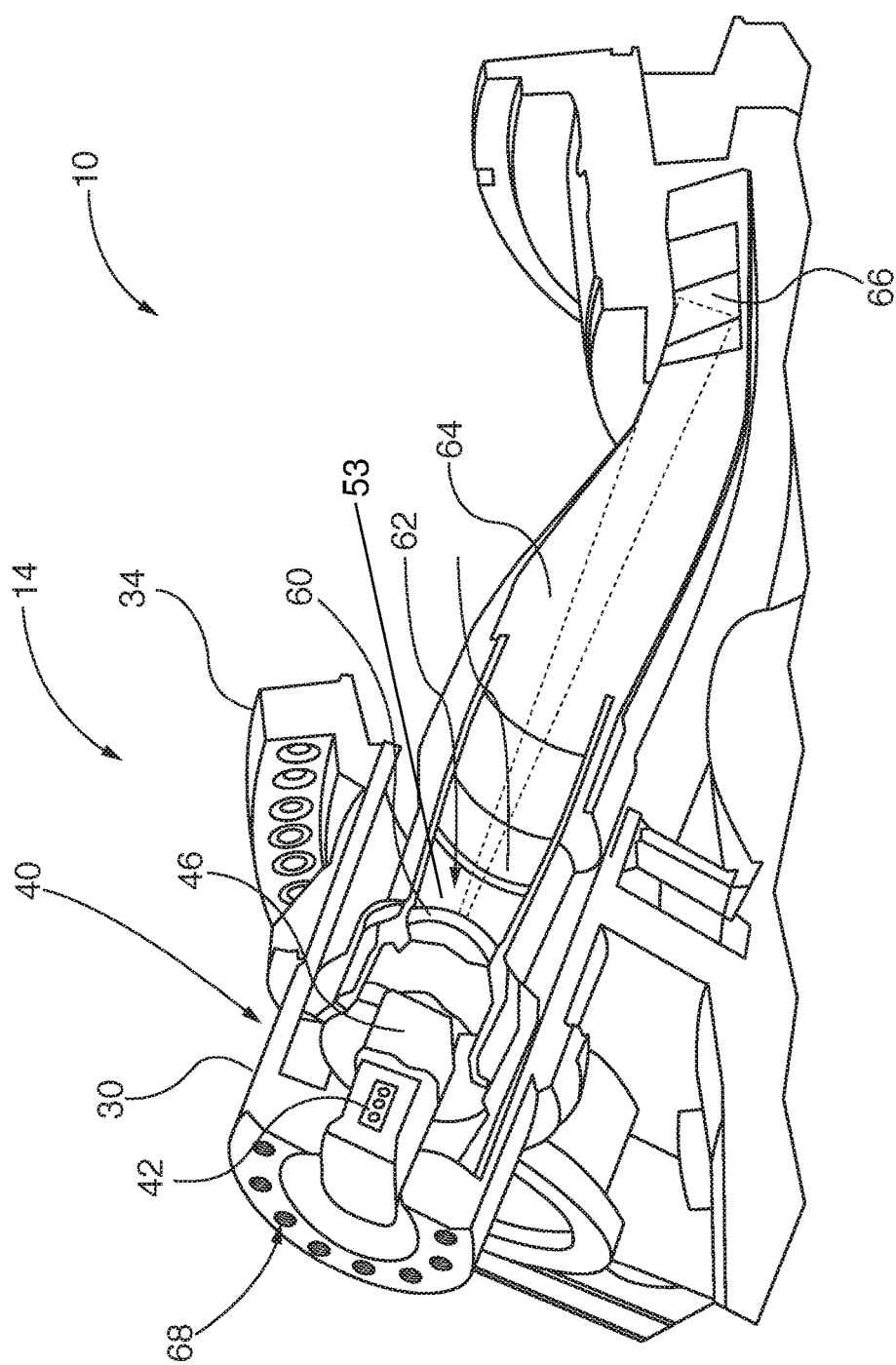
FIG. 4 is a partial cross sectional view of the turbine wherein the flash thermography device is shown located in a top hat portion of a combustor.

The device 40 is configured to capture IR images of internal portions of a turbine 10. For example, as previously described, the combustion section 14 includes a plurality of combustors 28 arrayed about the combustion section 14 that are in fluid communication with a combustion section 14 interior. Each combustor 28 includes a top hat portion 30 and a removable support housing 32. Referring to FIG. 4, a partial cross sectional view of the turbine 10 is illustrated wherein a selected support housing 32 is shown removed. Removal of the support housing 32 provides access to an opening 53 in the turbine 10 and thus a view of internal portions of the turbine 10. In accordance with an aspect of the invention, the device 40 is configured to capture IR images of internal portions of a turbine 10 as viewed through the opening 53 in the turbine 10. In an embodiment, a view of internal portions of the turbine 10 is available through an opening 53 such as found in a pilot cone 60 of a combustor basket portion 62. In accordance with the invention, the device 40 is sized to enable positioning of the device 40 in a recess of the top hat portion 30 such that the lens 44 is located adjacent to the opening 53 in the pilot cone 60. This enables the capturing of IR images of internal components of the turbine 10 as viewed by the device 40 through the opening 53 in pilot cone 60, for example, that are within a line of sight 64 (shown as dashed lines) of the device 40 such as at least one row 1 vane 66. In an embodiment, the device 40 may be affixed by a mounting fixture using preexisting apertures 68 used for securing a support housing 32. Alternatively, the device 40 may be hand held by an operator. It is understood that other openings in the turbine 10 may be used to capture IR images of internal portions of the turbine 10.

In order to obtain an IR image of a component such as vane 66, the flash source 50 is energized by the flash power supply 54 thereby causing the flash source 50 to emit a light pulse that heats the vane 66. For example, the flash source 50 provides approximately 5000 to 6000 Joules of energy output to heat at least one vane 66. The duration of light pulse may depend on the thickness of a BC or TBC layer being inspected on vane 66. A portion of the thermal energy radiated by the vane 66 is then detected by the IR sensor 42. The IR sensor 42 generates IR images of the vane 66 based on the thermal energy radiated by the vane 66. The length of time used for detecting the radiated thermal energy (i.e. signal collection time) is dependent upon the characteristics of the component that is being imaged. Thus, in the current embodiment of the invention, IR images of internal turbine components, such as row 1 vanes 66, are obtained non-intrusively and without removal of the main casing 34 of the turbine 10. In accordance with aspects of the invention, other components along a turbine a hot gas path may also be imaged such as transition components, blades and others.

It has been found by the inventors herein that IR images of a component obtained by the device 40 provide sufficient detail of the component to enable evaluation by an inspection/evaluation team. Further, the device 40 generates IR images having sufficient detail to enable determination of a thickness of a BC or TBC layer formed on a component using known methods. Therefore, the current invention enables nondestructive evaluation (NDE) of turbine components. If there is significant damage to the BC/TBC layers, the inspection/evaluation team can quickly make a decision to call for maintenance in order to avoid damage of a turbine component due to loss of BC/TBC layers. In addition, the disclosure of U.S. application Ser. No. 14/684,471, filed on Apr. 13, 2015, entitled SYSTEM TO PROGNOSE GAS TURBINE REMAINING USEFUL LIFE to Iyer et al. is hereby incorporated by reference in its entirety.

Figure 5:
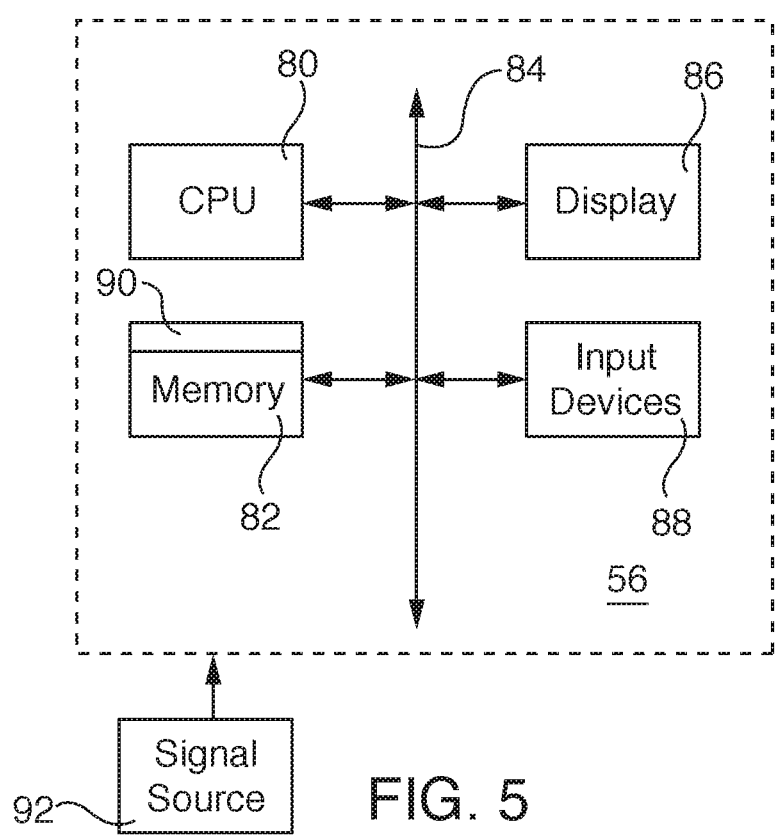
FIG. 5 is a high-level block diagram of a computer.

Referring back to FIG. 3, the IR sensor 42 is communicatively coupled to the computer 56 by electrical connection 58 or a wireless connection. The computer 56 includes software and drivers for controlling operation of the IR sensor 42, flash power supply 54 and flash source 50. The computer 56 may use well-known computer processors, memory units, storage devices, computer software, and other components. A high-level block diagram of such a computer is illustrated in FIG. 5. Computer 56 may include a central processing unit (CPU) 80, a memory 82 and an input/output (I/O) interface 84. The computer 56 is generally coupled through the I/O interface 84 to a display 86 for visualization and various input devices 88 that enable user interaction with the computer 56 such as a keyboard, keypad, touchpad, touchscreen, mouse, speakers, buttons or any combination thereof. Support circuits may include circuits such as cache, power supplies, clock circuits, and a communications bus. The memory 82 may include random access memory (RAM), read only memory (ROM), disk drive, tape drive, etc., or a combination thereof. Embodiments of the present disclosure may be implemented as a routine 90 that is stored in memory 82 and executed by the CPU 80 to process the signal from a signal source 92. As such, the computer 56 is a general purpose computer system that becomes a specific purpose computer system when executing the routine 90. The computer 56 can communicate with one or more networks such as a local area network (LAN), a general wide area network (WAN), and/or a public network (e.g., the Internet) via a network adapter. One skilled in the art will recognize that an implementation of an actual computer could contain other components as well, and that FIG. 5 is a high level representation of some of the components of such a computer for illustrative purposes.

The computer 56 also includes an operating system and micro-instruction code. The various processes and functions described herein may either be part of the micro-instruction code or part of the application program (or a combination thereof) which is executed via the operating system. In addition, various other peripheral devices may be connected to the computer platform such as an additional data storage device and a printing device. Examples of well-known computing systems, environments, and/or configurations that may be suitable for use with computer 56 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

In some examples, the computer 56 is disposed within and considered a part of IR sensor 42 or display 86. In still other examples, the computer 56 may be co-located in both IR sensor 42 and display 86. In some examples, full 2D images of a component such as a vane 66, that is, composite 2D images that include all 360 degrees or some other desired portion of the external surfaces of the vane 66 are compiled from a plurality of individual images or exposures obtained by IR sensor 42 for subsequent inspection by a qualified NDE inspector/operator. In addition, in some examples, the computer 56 is configured to combine a plurality of images of the vane 66 captured by IR sensor 42, and form a composite image reflecting the image data of each of the plurality of images.

While particular embodiments of the present disclosure have been illustrated and described, it would be obvious to those skilled in the art that various other changes and modifications can be made without departing from the spirit and scope of the disclosure. It is therefore intended to cover in the appended claims all such changes and modifications that are within the scope of this disclosure.

What is claimed is:

1. A flash thermography device for generating an infrared image of a turbine component located inside a turbine, comprising:
   a flash enclosure having an aperture;
   a flash tube located in the aperture, wherein the flash tube generates a light pulse that heats the turbine component; and
   an infrared sensor for detecting thermal energy radiated by the turbine component wherein the radiated thermal energy is transmitted through the aperture to the infrared sensor to enable generation of the infrared image, wherein the flash tube is annular and wherein the infrared sensor is positioned to receive thermal energy that passes through an annular opening defined by the flash tube.

2. The device according to claim 1, wherein the infrared sensor captures at least one image through an opening (53) in the turbine.

3. The device according to claim 2, wherein the opening is through a pilot cone (60) of a turbine combustor.

4. The device according to claim 1, wherein the infrared sensor captures at least one image of at least one vane of the turbine.

5. The device according to claim 1, wherein the component includes a thermal barrier coating and/or a bond coating.

6. A flash thermography device for generating an infrared image of a turbine component located inside a turbine, comprising:
   a flash enclosure;
   a flash source located in the flash enclosure, wherein the flash source is annular and defines an annular opening, the flash source operable to generate a light pulse that heats the turbine component;
   a conical reflector positioned substantially within the annular opening and defining a reflector opening;
   a lens positioned substantially within the reflector opening; and
   an infrared sensor for detecting thermal energy radiated by the turbine component through an opening in the turbine, wherein the radiated thermal energy is transmitted through the lens to the infrared sensor to enable generation of the infrared image.

7. The device according to claim 6, wherein the flash source is a flash tube.

8. The device according to claim 6, wherein the opening is through a pilot cone of a turbine combustor.

9. The device according to claim 6, wherein the infrared sensor captures at least one image of at least one vane of the turbine.

10. The device according to claim 6, wherein the component includes a thermal barrier coating and/or a bond coating.

11. A method for thermographically inspecting a turbine component located inside a turbine, comprising:
    providing a flash enclosure having an aperture;
    positioning a flash tube within the flash enclosure, wherein the flash tube generates a light pulse that heats the turbine component, and wherein the flash tube is annular and defines an annular opening;
    providing an infrared sensor for detecting thermal energy radiated by the turbine component, wherein the radiated thermal energy is transmitted through the aperture and through the annular opening to the infrared sensor to enable generation of the infrared image;
    locating the flash enclosure in a top hat section of a turbine combustor;
    capturing at least one image of the turbine component through an opening in the turbine combustor; and
    inspecting a turbine component characteristic.

12. The method according to claim 11, wherein the opening is through a pilot cone of the turbine combustor.

13. The method according to claim 11, wherein the infrared sensor captures at least one image of at least one vane of the turbine.

14. The method according to claim 11, wherein the flash enclosure includes a reflector.

15. The method according to claim 14, wherein the reflector is conical.

* * * * *